(12) United States Patent
Matsui (10) Patent No.: US 6,551,237 B2
(45) Date of Patent: Apr. 22, 2003

(54) CENTERING MECHANISM FOR CONTROLLING THE BENDING OF AN ELECTRICALLY BENDABLE ENDOSCOPE, AND AN ENDOSCOPE SYSTEM

(75) Inventor: Koichi Matsui, Koganei (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/123,784

(22) Filed: Apr. 16, 2002

(65) Prior Publication Data

US 2002/0165430 A1 Nov. 7, 2002

(30) Foreign Application Priority Data

Apr. 24, 2001 (JP) ........................................ 2001-126231

(51) Int. Cl.[7] ................................................. A61B 1/00
(52) U.S. Cl. ....................... 600/118; 600/145; 600/146; 600/150
(58) Field of Search ................................. 600/118, 145, 600/146, 150; 604/95.04, 95.05

(56) References Cited

U.S. PATENT DOCUMENTS 4,982,725 A * 1/1991 Hibino et al. ............... 600/117

5,347,989 A 9/1994 Monroe et al.

FOREIGN PATENT DOCUMENTS

JP 5-15486 * 1/1993 ............ A61B/1/00

* cited by examiner

Primary Examiner—John Mulcahy
(74) Attorney, Agent, or Firm—Scully, Scott, Murphy & Presser (57) ABSTRACT

According to the centering mechanism of this invention for an electrically bendable endoscope, the control circuit, in response to an instruction for centering, computes residual bending angles in U/D and L/R directions based on the values obtained as a result of feeding values indicated by the U/D and L/R potentiometers to an A/D converter. The control circuit conducts bending angle adjustment by bending the tip of the endoscope in directions appropriate to cancel out residual bending angles: for example, if the tip has been bent upward immediately before the centering switch is activated, the control circuit causes the tip to be bent downward, and if the tip has been bent leftward immediately before the centering switch is activated, the control circuit causes the tip to be bent rightward. Then, the bending angle is adjusted to zero.

6 Claims, 7 Drawing Sheets

CENTERING MECHANISM FOR CONTROLLING THE BENDING OF AN ELECTRICALLY BENDABLE ENDOSCOPE, AND AN ENDOSCOPE SYSTEM

This application claims benefit of Japanese Application No. 2001-126231 filed in Japan on Apr. 24, 2001, the contents of which are incorporated by this reference.

BACKGROUND OF THE INVENTION

1. Field of the Invention

The present invention relates to a centering mechanism of an electrically bendable endoscope, and an endoscope system, more specifically to a centering mechanism of an electrically bendable endoscope characterized by having a bending control portion at a bending segment, and to an endoscope system in which the bending of an electrically bendable endoscope is controlled.

2. Related Art Statement

Recently, endoscopes for examining the cavity of a hollow tube come to be widely used in medicine and in industries. When such an endoscope is used, the tip of its slender insertion segment is bent and inserted into the cavity of a hollow test tube. Bending the tip is achieved by directing bending effectors installed at the tip upward, downward, leftward or rightward appropriately via wires attached to the effectors.

Recently, an endoscope in which bending a bending segment is electrically achieved via wires attached to the segment through the driving of a motor installed close to the operator's hand is proposed, for example, in EP0587506A1.

According to the conventional motor driving mechanism for bending the tip of an endoscope, it is necessary to connect wires to an actuator such as a motor for bending the tip, and, in order to insert the tip into a hollow test tube, to straighten the tip of the endoscope and to direct it squarely towards the mouth of the tube.

Thus, the tip of an endoscope should achieve a centering before insertion: the tip makes a continuous spiral turn, with the radii of sequential spirals being gradually decreased, until the tip is straightened and aligned with the mouth of a hollow test tube.

However, centering effected in the conventional endoscope has following problems. Namely, it is often impossible to straighten the tip of the endoscope so as to align it with the mouth of a hollow test tube because of inherent slackness and redundant lengths due to previous repeated over-stretching of the wires even if the tensions of the wires have been adjusted to 0 (zero) via an actuator. Moreover, if centering is effected in a limited space, the tip of the endoscope might bump against the surrounding tissue. In addition, centering might take an undue long time in such a space.

OBJECTS AND SUMMARY OF THE INVENTION

Accordingly, it is an object of this invention to provide a centering mechanism for an electrically bendable endoscope by which the tip of an endoscope can be straightened and aligned with the mouth of a hollow test tube at one stroke of motion, without being exposed to the risk of bumping against the surrounding tissue even when the centering is performed in a limited space.

It is another object of this invention to provide an endoscope system in which the tip of an endoscope can be straightened and aligned with the mouth of a hollow test tube at one stroke of motion, without being exposed to the risk of bumping against the surrounding tissue even when the centering is performed in a limited space.

The centering mechanism for an electrically bendable endoscope according to this invention comprises a bending segment attached to the endoscope, a driving unit for bending the bending segment, a bending instruction unit for giving an instruction for bending the bending segment, a centering instruction feeding unit for causing the previously bent bending segment to be returned to a straightened state, and a control unit which controls, in response to an instruction from the centering instruction feeding unit, the driving unit so as to cause the bending segment to be bent in a reverse direction to the currently bent state introduced in response to a previous instruction from the bending instruction unit, and then to be bent in a specified direction by a specified amount.

Other features and benefits brought about by this invention will become thoroughly apparent by referring to the following explanation.

BRIEF DESCRIPTION OF THE DRAWINGS

FIGS. 1 to 7 relate to a first embodiment of this invention.

FIGS. 8 and 9 relate to a second embodiment of this invention.

DETAILED DESCRIPTION OF THE PREFERRED EMBODIMENTS

Figure 1:
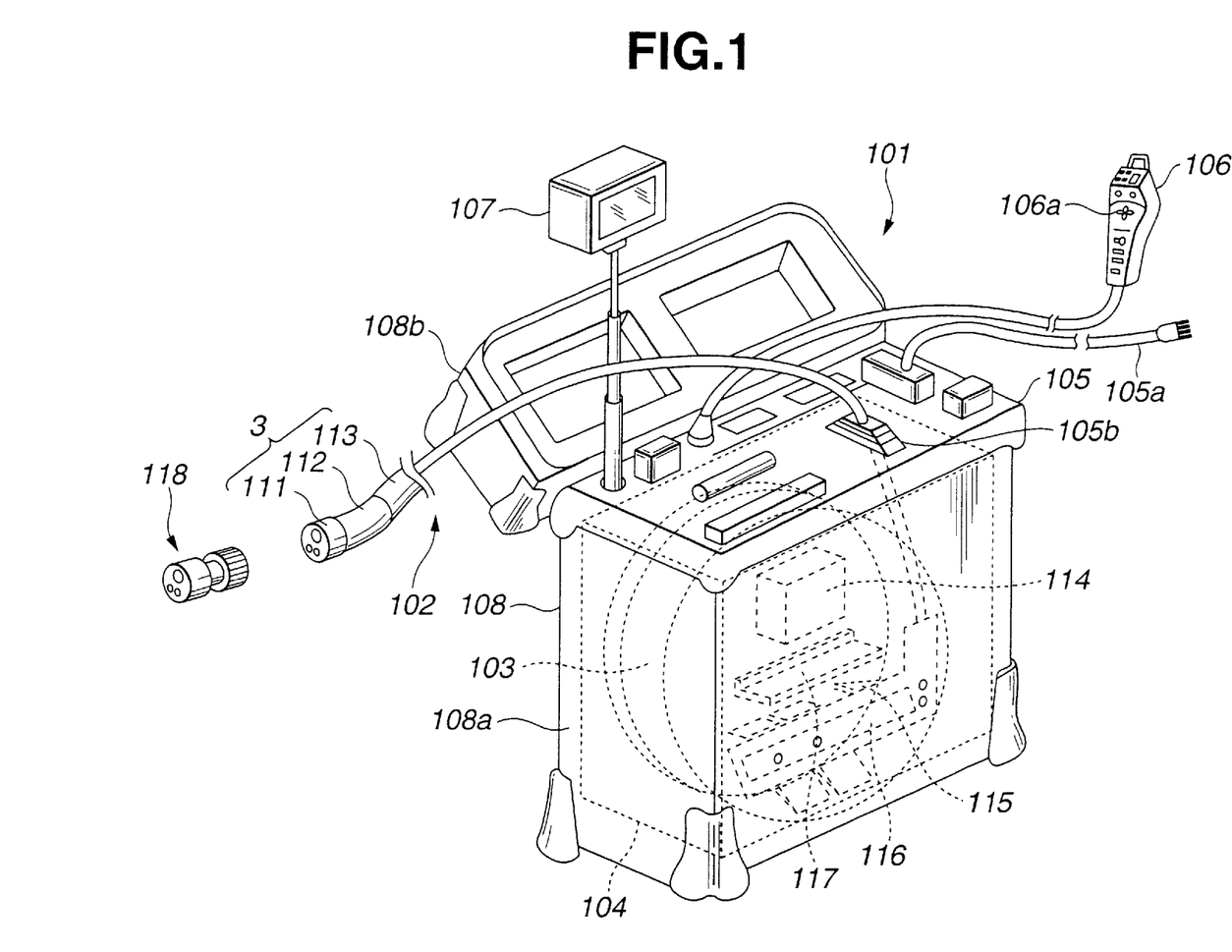
FIG. 1 is an overview showing the overall composition of an endoscope system representing a first embodiment of this invention.

First Embodiment:

As shown in FIG. 1, an endoscope system 101 representing a first embodiment of this invention comprises an endoscope 102 (to be referred to as electrically bendable endoscope hereinafter) for industrial use equipped with a flexible, slender insertion segment 3; a cylindrical drum unit 103 for withdrawing the insertion segment 3 of the electrically bendable endoscope 102 by taking up a cord connected to the endoscope and winding it around its periphery; a frame unit 104 for rotatably stabilizing the drum unit 103; a front panel 105 attached to the top of the frame unit 104 which carries various switches and connectors, and supply and exhaust ducts on its surface; a remote controller 106 which is capable of being freely connected to or disconnected from the front panel 105 via a cable; a monitor freely rotatably attached to the top of a stand which can freely extend or contract; a housing 108 which contains buffers for moderating mechanical impacts inadvertently imposed on equipment kept within; and an AC cable 105a connected to the front panel 105 for providing the system with power from a commercial power source. The housing 108 consists of a base body 108a which constitutes the housing body itself, and a lid body 108b.

The insertion segment 3 of the electrically bendable endoscope 102 extends from the front panel 105 externally through a rubber member 105b which is installed for preventing the segment in question from being unduly bent due to its own weight. The insertion segment 3 comprises, from its tip end in order, a rigid tip end 111, a bending portion 2 which is attached to the rear end of the tip end 111 for directing the tip end towards a desired direction, and a slender, flexible tube unit 113.

The drum unit 103 comprises, in its interior, a light source unit 114 which transmits illuminating light to a light guide serving as an illuminating light transmitting means of the electrically bendable endoscope 102; a CCU 115 for processing signals from an imaging element installed at the tip end 11 of the endoscope insertion segment 3; a drive unit 116 for electrically bending the bending portion 2 of the endoscope insertion segment 3; and a control unit 117 for controlling the operation of the drive unit 116. The remote controller 106 has a joystick 106a which serves as a bending input feeding portion for feeding input necessary for bending the bending portion 3 of the endoscope insertion segment 3.

Various optical adapters 118 can be freely attached to or detached from the tip end 111 of the endoscope insertion segment 102a, so as to alter the optical characteristics as appropriate including the visual direction, visual angle, etc.

Figure 2:
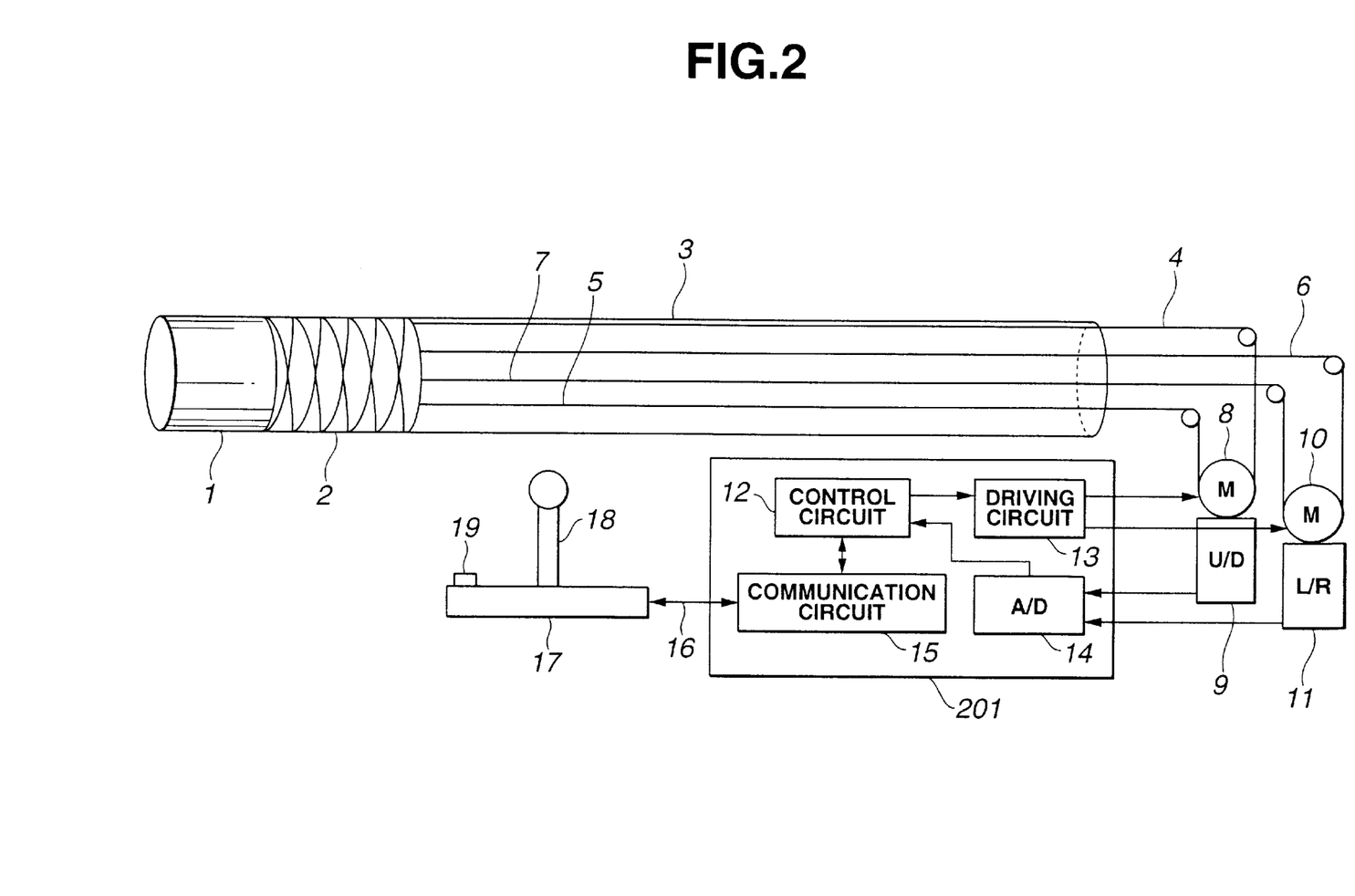
FIG. 2 shows the composition of an electrically bendable endoscope of the system of FIG. 1.

As shown in FIG. 2, the tip end 1 of the electrically bendable endoscope 102 of this embodiment is connected via the bending portion 2 to the insertion segment 3.

The insertion segment 3 comprises, in its interior, an UP angle wire 4 for bending the bending portion 2 upward to cause the visual field to turn upward; a DOWN angle wire 5 to cause the visual field to turn downward; a RIGHT angle wire 6 to cause the visual field to turn rightward; and a LEFT angle wire 7 to cause the visual field to turn leftward.

The proximal ends of the UP and DOWN angle wires 4 and 5 are connected to a U/D motor 8, while those of the RIGHT and LEFT angle wires 6 and 7 are connected to an L/R motor 10. A U/D potentiometer 9 is co-axially connected to the U/D motor 8 while an L/R potentiometer 11 co-axially connected to the L/R motor 10.

The U/D and L/R motors 8 and 10 are connected to a driving circuit 13 of the electrical bending effecting circuit unit 201, while the U/D and L/R potentiometers 9 and 11 are connected to an A/D converter 14 of the electrical bending effecting circuit unit 201.

To a communication circuit 15 of the electrical bending effecting circuit unit 201 is connected an operation unit 17 via a communication line 16. The operation unit 17 comprises a joystick 18 for effecting bending operation; a centering switch 19 for initiating centering operation; and other functional switches not illustrated here. A control circuit 12 of the electrical bending effecting circuit unit 201 receives output from the A/D converter 14, and controls the communication circuit 15 and the driving circuit 13.

Next, the operation of this embodiment configured as above will be described.

Figure 3:
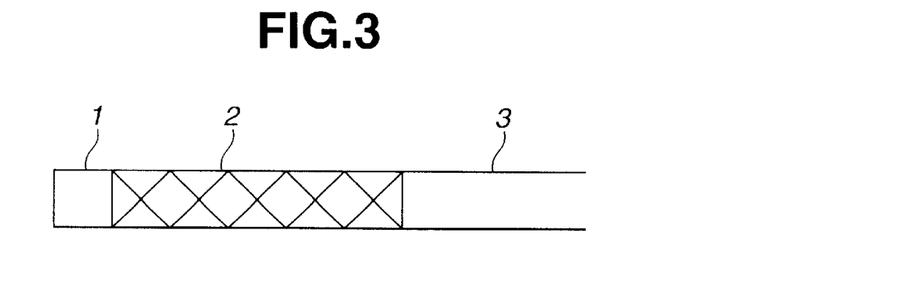
FIG. 3 is a first illustration showing the operation of the electrically bendable endoscope of FIG. 2.
Figure 4:
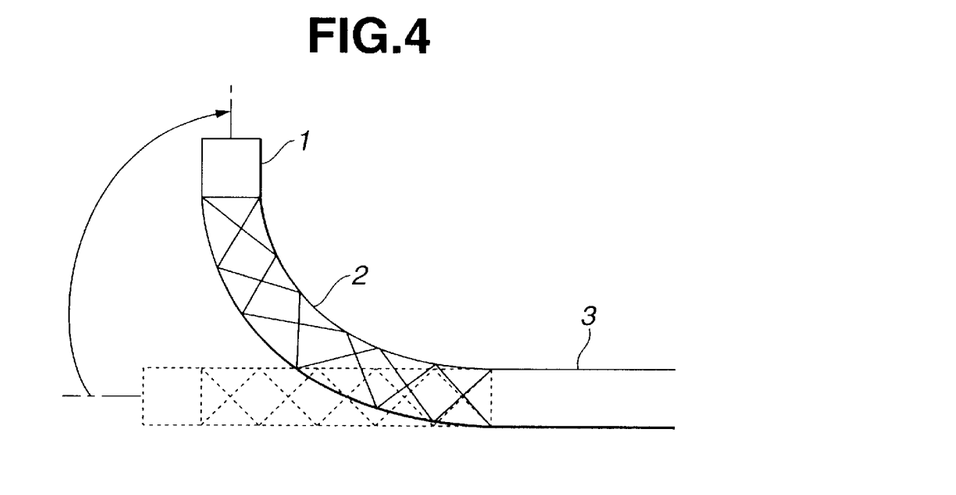
FIG. 4 is a second illustration showing the operation of the electrically bendable endoscope of FIG. 1.

The operator holds the insertion segment 3, and inserts its tip end 1 into the mouth of a hollow test tube to reach a target site to be examined. Then, the operator manipulates the joystick 18 attached to the operation unit 17, so as to direct the tip end 1 upward, downward, leftward or rightward as appropriate to completely visualize the target site, as shown in FIGS. 3 and 4.

Information regarding how the joystick 18 is manipulated is fed via the communication line 16 to the communication circuit 15. The control circuit 12, based on the information provided via the communication circuit 15, controls the operation of the U/D and L/R motors 8 and 10.

The U/D and L/R motors 8 and 10 have the UP and DOWN angle wires 4 and 5, and the RIGHT and LEFT angle wires 6 and 7 connected thereto respectively. The UP and DOWN angle wires 4 and 5, and the RIGHT and LEFT angle wires 6 and 7 pass through the insertion segment 3, so as to activate the bending portion 2.

When it is required to bend the tip end 1 upwards in the visual field, the control circuit 12 only needs to control the driving circuit 13 so as to cause the UP angle wire 4 to be pulled towards the U/D motor 8 from the tip end 1. In a similar manner, it is possible to direct the tip end 1 downward, or rightward or leftward by pulling the DOWN angle wire 5 towards the U/D motor 8, or by pulling the RIGHT or LEFT angle wire 6 or 7 towards the L/R motor 10.

The U/D and L/R potentiometers 9 and 11 are connected to the U/D and L/R motors 8 and 10 respectively, and values indicated by the U/D and L/R potentiometers are subjected to A/D conversion via an A/D converter 14 so that the rotation magnitudes of the U/D and L/R motors 8 and 10 can be determined.

Pulls applied to the UP, DOWN, RIGHT and LEFT angle wires 4, 5, 6 and 7 are adjusted in a feedback manner based on the rotation magnitudes thus determined. This makes it possible for the tip end 1 to be precisely directed towards a target site to be examined as shown in FIG. 4.

To prevent the fluctuation of the tip end 1 after the tip end 1 has been precisely directed towards a target site, the acceptable values of the U/D and L/R potentiometers 9 and 11 are allowed to have certain redundancies depending on the characteristics of the U/D and L/R motors 8 and 10, and of the UP, DOWN, RIGHT and LEFT angle wires 4, 5, 6 and 7.

When it is required to alter the position of the tip end 1 in a cavity including a target site, the operator takes his hand off from the joystick 18 of the operation unit 17, holds the insertion segment 3, and withdraws the tip end 1.

Figure 5:
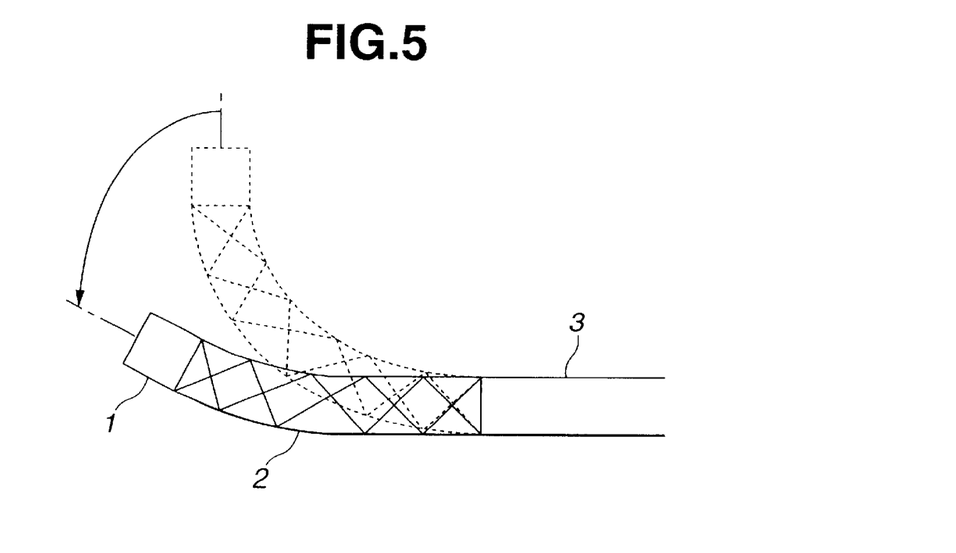
FIG. 5 is a third illustration showing the operation of the electrically bendable endoscope of FIG. 1.

During the process, however, even when pulls applied to the UP, DOWN, RIGHT and LEFT angle wires are reduced to zero, the tip end 1 may not be made sufficiently straight to be aligned with the insertion segment 3 as shown in FIG. 5, on account of the mechanical property of the bending portion 2, and of the control redundancy permitted to the U/D and L/R potentiometers 9 and 11.

To meet the situation, the operator activates a centering switch 19 of the operation unit 17. A centering instruction delivered through the activation of the centering switch 19 is fed via the communication line 16 and communication circuit 15 to the control circuit 12.

Figure 6:
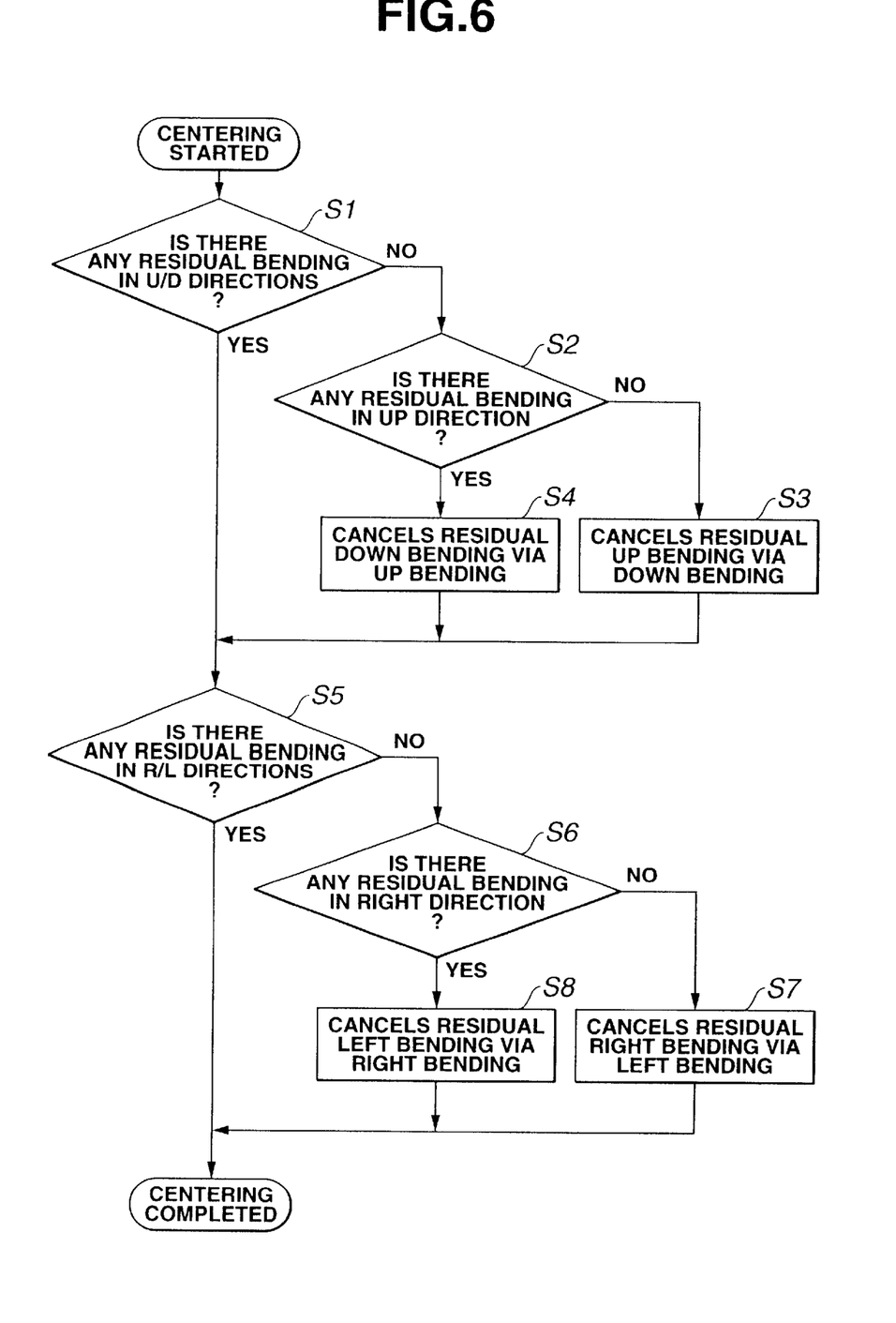
FIG. 6 is a flowchart showing the flow of steps taken by the control circuit of FIG. 2 for effecting centering.

In response to the centering instruction, the control circuit 12 initiates control steps as shown in FIG. 6: it determines by calculation residual bending angles in U/D and L/R directions, based on the values obtained by subjecting the values of U/D and L/R potentiometers 9 and 11 to A/D conversion via the A/D converter 14. Namely, the residual angle of the tip end 1 to the insertion segment 3 is estimated based on the values indicated by the U/D and L/R potentiometers 9 and 11.

Specifically, at step S1, the control circuit 12 checks if the tip end 1 has any residual angle in U/D directions to the insertion segment 3. If indeed the tip end 1 is bent in U/D directions with respect to the insertion segment 3 immediately before the centering switch 19 is activated, the control circuit 12 determines there is a residual angle in a U/D direction, and proceeds to step S2 at which it checks if the tip end 1 has any residual angle in the UP direction to the insertion segment 3.

If indeed the tip end 1 is bent in the UP direction immediately before the centering switch 19 is activated, the control circuit 12 determines there is a residual angle in the UP direction. At step S3, the control circuit 12 causes the tip end 1 to be sufficiently bent in the DOWN direction to cancel the residual bending in the UP direction. Alternatively, if there is a residual bending in the DOWN direction immediately before the centering switch 19 is activated, the control circuit 12 determines there is no residual bending in the UP direction, i.e., there is a residual bending in the DOWN direction at step S2, and causes the tip end 1 to be bent in the UP direction so as to cancel the downward residual bending at step S4.

On the other hand, when the control circuit 12 determines there is no residual bending in the U/D directions, it proceeds to step S5, at which it checks if there is any residual bending in the L/R directions. If indeed there is a residual bending in the L/R directions immediately before the centering switch 19 is activated, the control circuit 12 determines there is a residual angle in an L/R direction. The control circuit 12 checks if there is any residual bending in the RIGHT direction at step S6. When the control circuit 12 determines there is no residual bending in the U/D directions at step S5, it ends the operation.

If there is indeed a residual rightward bending immediately before the centering switch 19 is activated, the control circuit 12 determines there is a residual bending in the RIGHT direction at step S6, causes the tip end 1 to be bent in the LEFT direction so as to cancel the residual bending in the RIGHT direction at step S7, to complete the operation.

Alternatively, if the tip end 1 has been bent leftward immediately before the centering switch 19 is activated, the central circuit 12 determines there is no residual bending in the RIGHT direction, i.e., there is a residual bending in the LEFT direction at step S6, and causes the tip end 1 to be bent in the RIGHT direction so as to cancel the residual leftward bending at step S8, to complete the operation.

As seen above, the control circuit 12 causes the tip end 1 to be bent in a direction reverse to a residual bending remaining on the tip end 1: for example, if the tip end 1 is bent upward immediately before the centering switch 19 is activated, the control circuit 12 will cause the tip end 1 to be bent downward, and if the tip end 1 is bent leftward immediately before the centering switch 19 is activated, the control circuit 12 will cause the tip end 1 to be bent rightward. The control circuit 12 then reduces the residual bending angle to zero. This operation will be continued as long as there is any residual angle in the UP or DOWN, or LEFT or RIGHT direction of the visual field.

Figure 7:
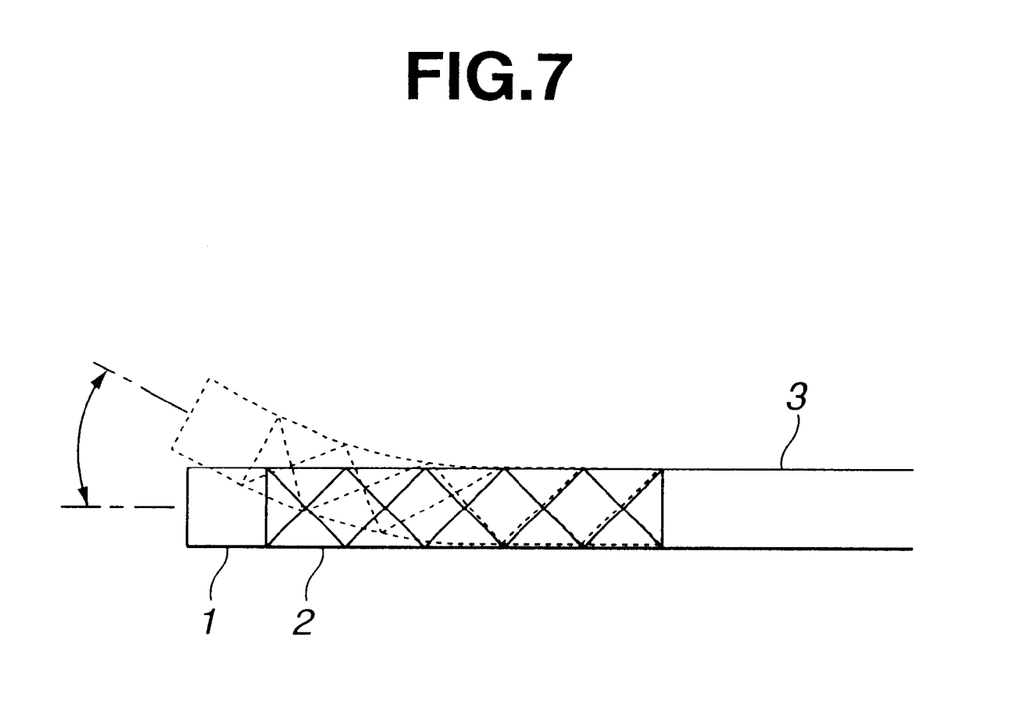
FIG. 7 is a fourth illustration showing the operation of the electrically bendable endoscope of FIG. 2.

As a consequence, the tip end 1 is precisely aligned, the bending portion 2 included, with the insertion segment 3 as shown in FIG. 7.

Alternatively, if the U/D and L/R potentiometers are made to act as encoders, it will be possible for their output to be directly fed to the control circuit 12 without the intervention of the A/D converter 14.

Second Embodiment:

Because the second embodiment is approximately the same with the first embodiment, only different features will be described and the corresponding elements will be represented by the same symbols, and their explanation will be omitted.

Figure 8:
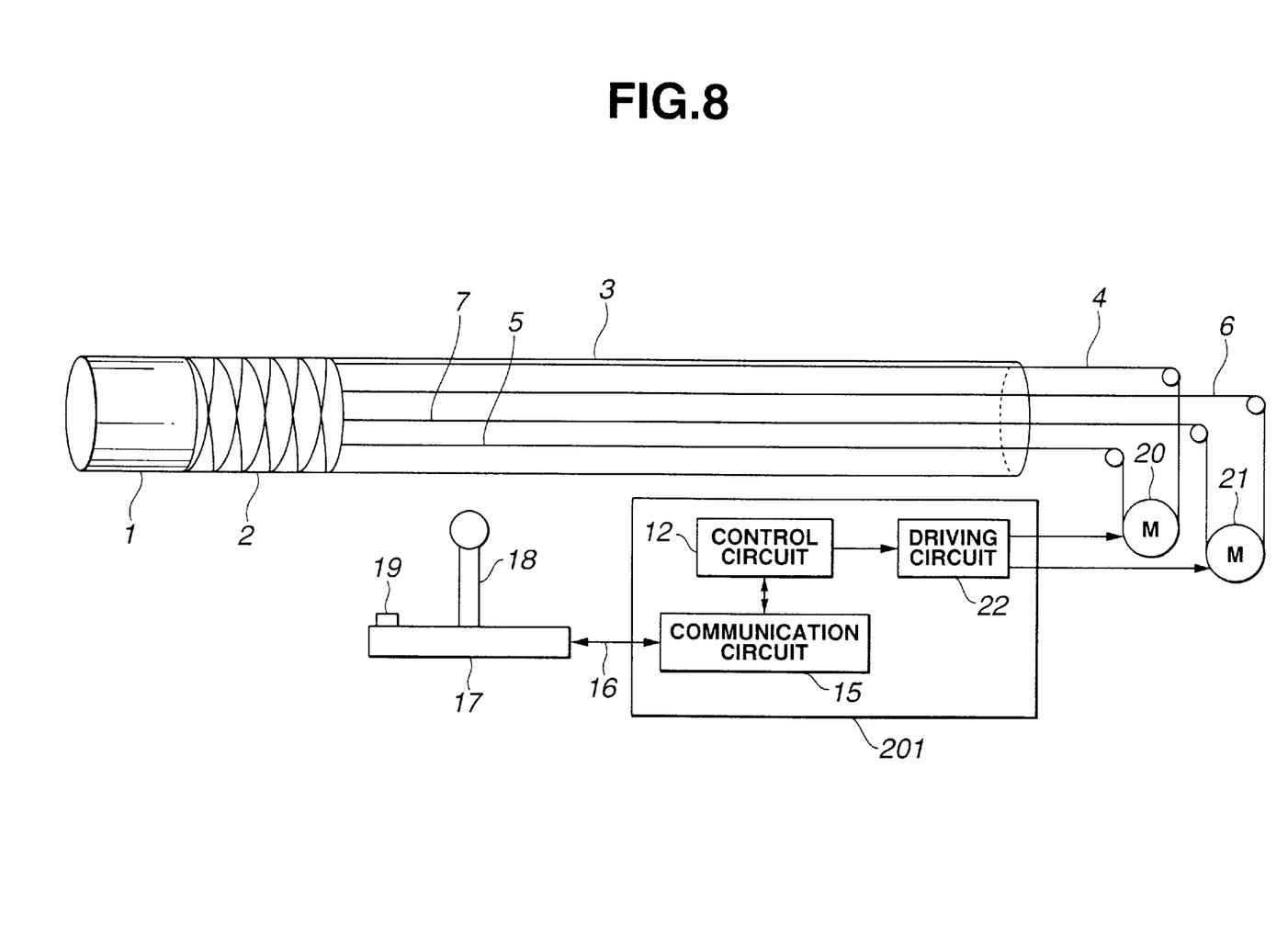
FIG. 8 shows the composition of an electrically bendable endoscope system.

The U/D motor 8 and potentiometer 9, and the L/R motor 10 and potentiometer 11 of the first embodiment are substituted for a U/D pulse motor 20 and a L/R pulse motor 21 respectively in this embodiment as shown in FIG. 8. Instead of the driving circuit 13, a pulse motor driving circuit 22 is introduced which is connected to the U/D and L/R pulse motors 20 and 21. The A/D converter 14 was omitted. The other configuration is the same with that of the first embodiment.

Instead of the feedback control, under which the bending angle of the bending portion 1 is controlled by activating via the driving circuit 13 the U/D and L/R motors 8 and 10 based on the output obtained by feeding the values of the U/D and L/R potentiometers 9 and 11 to the A/D converter 14, a feed forward control is introduced in this embodiment which is based on the number of pulses delivered to the U/D and L/R pulse motors 20 and 21. The other normal operation than this is similarly controlled as in the first embodiment.

Although in the first embodiment the tip end 1 is controlled so as to keep its position within a tolerable range, to relieve the tip end from fluctuations, the second embodiment can dispense with such a tolerable range, because it depends on a feed forward control. Thus, with the second embodiment, residual bending angles may result from laxes developed in RIGHT and LEFT angle wires 6 and 7 and others, and at the insertion segment 3 which have undergone repeated stretching and contracting.

Figure 9:
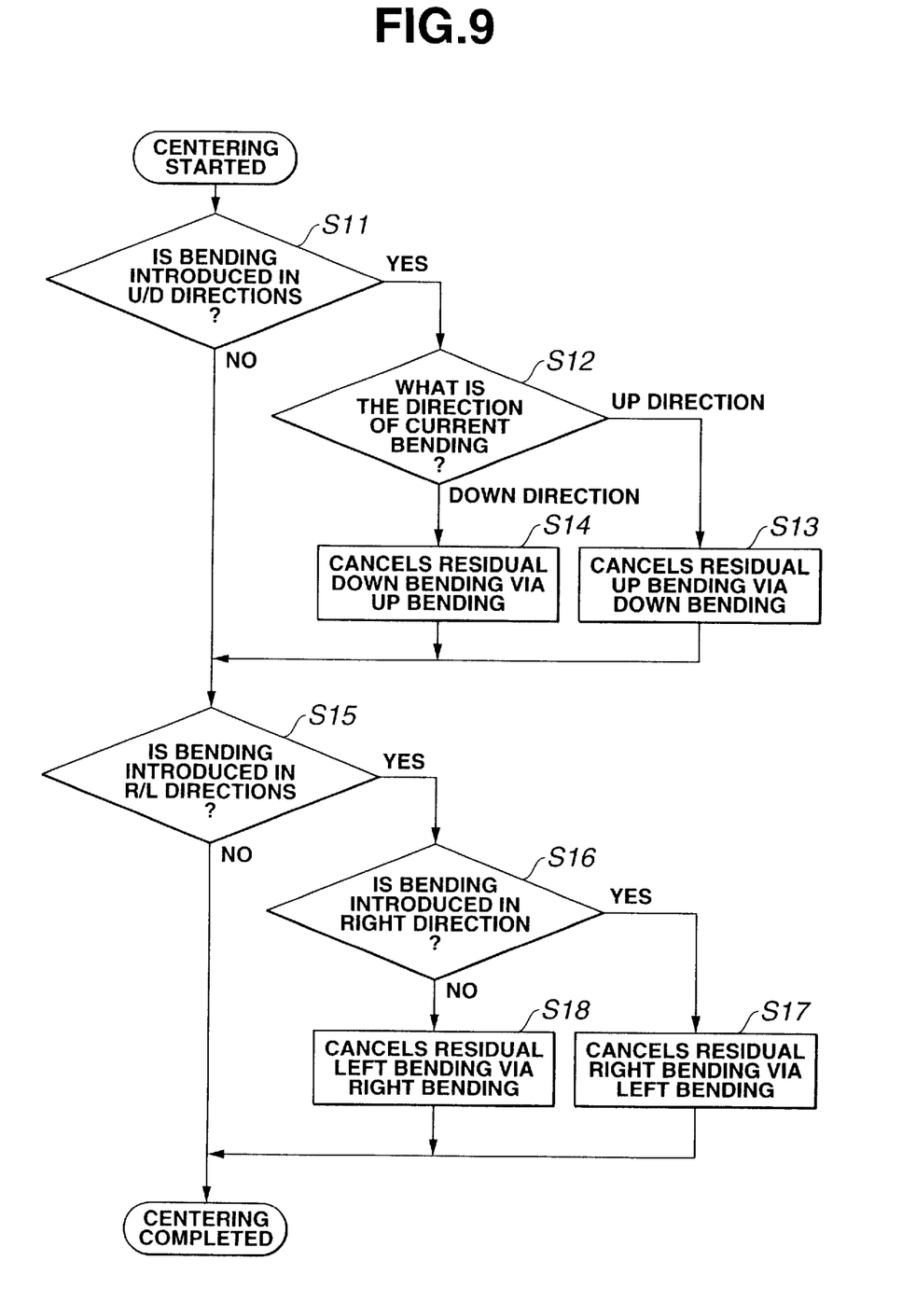
FIG. 9 a flowchart showing the flow of steps taken by the control circuit of FIG. 8 for effecting centering.

When it is required to straighten the tip end 1 for centering after having bent it, the control circuit 12 will normally take the steps as shown in the flowchart of FIG. 9. Immediately before it receives a centering instruction, the control circuit 12 estimates the angle and direction of a residual bending resulting from involved slackened wires if present, by checking the position of the tip end 1. Then, the control circuit 12 causes the tip end 1 to be bent in a direction reverse to the residual bending: for example, if the tip end 1 is bent upward immediately before the centering switch 19 will be activated, the control circuit 12 will cause the tip end 1 to be bent downward, and if the tip end 1 is bent leftward immediately before the centering switch 19 will be activated, the control circuit 12 will cause the tip end 1 to be bent rightward. The control circuit 12 conducts this operation so as to reduce the residual bending angle to zero. This operation will be conducted as long as there is any residual angle in the UP or DOWN, or LEFT or RIGHT direction of the visual field.

To put it specifically, as shown in FIG. 9, the control circuit 12 initially checks if the tip end 1 has been bent in U/D directions immediately before the centering switch 19 is activated at step S11. If it finds the tip end 1 has been bent in U/D directions, it determines there is a residual bending in U/D directions, and determines the direction of the residual bending immediately before the centering switch 19 is activated, at step S12.

If the tip end 1 is bent upward immediately before the centering switch 19 is activated, the control circuit 12 determines there is a residual UPWARD bending at step S12, it causes the tip end 1 to be bent downward at step 13, thereby canceling the residual upward bending. Alternatively, if there is a residual downward bending immediately before the centering switch 19 is activated, the control circuit 12 determines there is no residual upward bending, i.e., there is a residual downward bending at step S12, and causes the tip end 1 to be bent upward, thereby canceling the downward bending at step S14.

If the control circuit 12 determines there is no bending in U/D directions at step S11, it proceeds to step S15 at which it checks if the tip end 1 has been bent in L/R directions immediately before the centering switch 19 is activated. If the control circuit 12 finds the tip end 1 has been bent in L/D directions, it determines there is a residual bending in the L/R directions, and checks how the tip end 1 is bent before the centering switch is activated at step S16. If the control circuit 12 determines there is no residual bending in the U/D directions at step S15, the control circuit 12 completes the operation.

Alternatively, if the control circuit 12 finds the tip end 1 has been bent rightward immediately before the centering switch 19 is activated, it determines there is a residual rightward bending at step 16, and causes the tip end to be bent leftward at step 17, thereby canceling the residual right bending. Then, the control circuit 12 completes the operation.

Alternatively, if the control circuit 12 finds the tip end 1 has been bent leftward immediately before the centering switch 19 is activated, it determines there is no residual rightward bending at step 15, i.e., there is a residual leftward bending, and causes the tip end to be bent rightward, thereby canceling the residual left bending at step S18. Then, the control circuit 12 completes the operation.

As a consequence, the tip end 1 is precisely aligned, the bending portion 2 included, with the insertion segment 3 as shown in FIG. 7.

It is apparent that preparing widely different embodiments will be possible by referring to the description of this invention without departing from the spirit and scope of this invention. This invention should not be limited by any particular embodiments except by the attended claims.

What is claimed is:

1. A centering mechanism of an electrically bendable endoscope comprising:

a bending portion introduced in the endoscope;
 a bending effecting unit for causing the bending portion to be bent;
 a bending instruction unit for giving an instruction for bending the bending portion;
 a centering instruction feeding unit for giving an instruction for returning the bent bending portion to a straight state; and
 a control unit which, in response to the instruction from the centering instruction feeding unit, controls the bending effecting unit, so that the bending portion is bent in a direction reverse to the direction in which said portion has been bent in response to the previous instruction from the bending instruction unit, and then causes the bending portion to be bent in a predetermined direction by a predetermined amount.

2. A centering mechanism of an electrically bendable endoscope comprising:

an instruction feeding unit for giving an instruction for straightening a scope end of the electrically bendable endoscope with respect to the mouth of a hollow test tube;
 a detection unit for detecting a bending angle of the electrically bendable endoscope in response to the instruction from the instruction feeding unit;
 a computation unit for computing a residual bending angle of the electrically bendable endoscope based on the detection result from the detection unit; and
 a bending controlling unit for causing the scope end to be bent in a direction reverse to the direction taken by the scope end immediately before centering, by an amount determined by the computation result.

3. A centering mechanism of an electrically bendable endoscope comprising:

an operation unit comprising an angle feeding unit for specifying a bending angle of a bending portion responsible for bending the tip of an endoscope which is connected via an angle wire to an electric actuator, and a centering instruction feeding unit; and
 a control unit for controlling the electric actuator based on an instruction from the operating unit,
 wherein the control unit, in response to input from the centering instruction feeding unit, temporarily causes the bending portion to be bent in a direction reverse to the bending direction taken by the bending portion immediately before the entry of the input, and then causes the bending portion to be straightened.

4. An endoscope system comprising:

an endoscope for obtaining an image of a site in a cavity of a hollow tube;
 a signal processing unit for processing image signals obtained by the endoscope;
 a bending portion introduced in the endoscope;
 a bending effecting unit for bending the bending portion;
 a bending instruction unit for giving an instruction for bending the bending portion;
 a centering feeding unit for giving an instruction for returning the bent bending portion to a straightened state; and
 a control unit which, in response to the instruction from the centering instruction feeding unit, controls the bending effecting unit, so that the bending portion is bent in a direction reverse to the direction in which said portion has been bent in response to the previous instruction from the bending instruction unit, and then causes the bending portion to be bent in a predetermined direction by a predetermined amount.

5. An endoscope system comprising:

an electrically bendable endoscope whose bending portion can be electrically bent for obtaining an image of a site in a cavity of a hollow tube;
 a signal processing unit for processing image signals obtained by the electrically bendable endoscope;
 an instruction feeding unit for giving an instruction for straightening a scope end of the electrically bendable endoscope with respect to the mouth of the hollow tube;
 a detection unit for detecting a bending angle of the electrically bendable endoscope in response to the instruction from the instruction feeding unit;
 a computation unit for computing a residual bending angle of the electrically bendable endoscope based on the detection result from the detection unit; and
 a bending controlling unit for causing the scope end to be bent in a direction reverse to the direction taken by the scope end immediately before centering, by an amount determined by the computation result.

6. An endoscope system comprising:

an endoscope for obtaining an image of a site in a cavity of a hollow tube; and
 a signal processing unit for processing image signals obtained by the endoscope, wherein
 the endoscope comprises:
  an operation unit comprising an angle feeding unit for specifying a bending angle of a bending portion responsible for bending the tip of an endoscope which is connected via an angle wire to an electric actuator, and a centering instruction feeding unit; and a control unit for controlling the electric actuator based on an instruction from the operating unit, wherein the control unit, in response to input from the centering instruction feeding unit, temporarily causes the bending portion to be bent in a direction reverse to the bending direction taken by the bending portion immediately before the entry of the input, and then causes the bending portion to be straightened.

* * * * *